US00PP22583P2

(12) United States Plant Patent
Bullis

(10) Patent No.: US PP22,583 P2
(45) Date of Patent: Mar. 13, 2012

(54) ***NEOREGELIA* PLANT NAMED 'SEDUCTION'**

(50) Latin Name: ***Noregelia* hybrid×*(Neoregelia carcharodon×Neoregelia carolinae)***
Varietal Denomination: Seduction

(75) Inventor: Patricia E. Gomez Bullis, Princeton, FL (US)

(73) Assignee: Bullis Bromeliads, Princeton, FL (US)

( * ) Notice: Subject to any disclaimer, the term of this patent is extended or adjusted under 35 U.S.C. 154(b) by 0 days.

(21) Appl. No.: 12/806,813

(22) Filed: Aug. 21, 2010

(51) Int. Cl.
*A01H 5/00* (2006.01)

(52) U.S. Cl. ..... Plt./370

(58) Field of Classification Search ..... Plt./370
See application file for complete search history.

*Primary Examiner* — June Hwu
(74) *Attorney, Agent, or Firm* — C. A. Whealy

(57) ABSTRACT

A new and distinct cultivar of *Neoregelia* plant named 'Seduction', characterized by its upright and outwardly arching growth habit; broad glossy brownish purple-colored lower leaves; broad glossy red purple-colored upper leaves; good interiorscape and landscape performance; resistance to *Exserohilium.*

1 Drawing Sheet

Botanical designation: *Neoregelia* hybrid×(*Neoregelia carcharodon*×*Neoregelia carolinae*)
Cultivar denomination: 'SEDUCTION'.

BACKGROUND OF THE INVENTION

The present invention relates to a new and distinct cultivar of *Neoregelia* plant, botanically known as *Neoregelia* hybrid× (*Neoregelia carcharodon*×*Neoregelia carolinae*), and hereinafter referred to by the name 'Seduction'.

The new *Neoregelia* plant is a product of a planned breeding program conducted by the Inventor in Princeton, Fla. The objective of the breeding program is to create new *Neoregelia* plants with uniquely colored leaves.

The new *Neoregelia* plant originated from a cross-pollination made by the Inventor in 2002 in Princeton, Fla. of *Neoregelia* hybrid 'Autumn Leaves', not patented, as the female, or seed, parent with an unnamed proprietary selection of *Neoregelia carcharodon*×*Neoregelia carolinae,* not patented, as the male, or pollen, parent. The new *Neoregelia* plant was discovered and selected by the Inventor as a single plant within the progeny of the stated cross-pollination in a controlled greenhouse environment in Princeton, Fla. in 2002.

Asexual reproduction of the new *Neoregelia* plant by offsets in a controlled environment in Princeton, Fla. since 2003, has shown that the unique features of this new *Neoregelia* plant are stable and reproduced true to type in successive generations.

SUMMARY OF THE INVENTION

Plants of the new *Neoregelia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Seduction'. These characteristics in combination distinguish 'Seduction' as a new and distinct cultivar of *Neoregelia:*

1. Upright and outwardly arching growth habit.
2. Broad glossy brownish purple-colored lower leaves.
3. Broad glossy red purple-colored upper leaves.
4. Good interiorscape and landscape performance.
5. Resistant to *Exserohilium.*

Plants of the new *Neoregelia* differ primarily from plants of the female parent, 'Autumn Leaves', in the following characteristics:

1. Plants of the new *Neoregelia* are denser than plants of 'Autumn Leaves'.
2. Plants of the new *Neoregelia* have shorter, broader and sturdier leaves than plants of 'Autumn Leaves'.
3. Plants of the new *Neoregelia* do not require flower bud initiation to develop leaf coloration whereas plants of 'Autumn Leaves' require flower bud initiation to develop leaf coloration.
4. Plants of the new *Neoregelia* are more disease resistant than plants of 'Autumn Leaves'.

Plants of the new *Neoregelia* differ primarily from plants of the male parent selection in the following characteristics:

1. Plants of the new *Neoregelia* are not as broad and have shorter leaves than plants of the male parent selection.
2. Plants of the new *Neoregelia* do not require flower bud initiation to develop leaf coloration whereas plants of the male parent selection require flower bud initiation to develop leaf coloration.
3. Plants of the new *Neoregelia* and the male parent selection differ in upper leaf coloration.
4. Marginal leaf spines of plants of the new *Neoregelia* are shorter than marginal leaf spines of plants of the male parent selection.

Plants of the new *Neoregelia* can be compared to plants of the *Neoregelia* 'Victoria Pink', not patented. In side-by-side comparisons conducted in Princeton, Fla., plants of the new *Neoregelia* and 'Victoria Pink' differed primarily in the following characteristics:

1. Root systems of plants of the new *Neoregelia* were stronger and denser than root systems of plants of 'Victoria Pink'.
2. Plants of the new *Neoregelia* had broader leaves than plants of 'Victoria Pink'.

3. Plants of the new *Neoregelia* and 'Victoria Pink' differed in leaf coloration.
4. Plants of the new *Neoregelia* were more resistant to leaf spotting during periods of hot and rainy weather than plants of 'Victoria Pink'.

BRIEF DESCRIPTION OF THE PHOTOGRAPHS

The accompanying colored photographs illustrate the overall appearance of the new *Neoregelia* plant showing the colors as true as it is reasonably possible to obtain in colored reproductions of this type. Colors in the photographs may differ slightly from the color values cited in the detailed botanical description which accurately describe the colors of the new *Neoregelia* plant.

The photograph at the bottom of the sheet is a side perspective view of a typical flowering plant of 'Seduction' grown in a container.

The photograph at the top of the sheet is a top perspective view of a typical flowering plant of 'Seduction'.

DETAILED BOTANICAL DESCRIPTION

The aforementioned photographs and following observations, measurements and values describe flowering plants grown during the spring in 15-cm containers in a polypropylene-covered greenhouse in Princeton, Fla. under commercial *Neoregelia* production practices. During the production of the plants, day temperatures ranged from 10° C. to 32° C., night temperatures ranged from 7° C. to 32° C. and light levels averaged 3,200 foot-candles. Plants were one year old when the photographs and description were taken. In the following description, color references are made to The Royal Horticultural Society Colour Chart, 2007 Edition, except where general terms of ordinary dictionary significance are used.

Botanical classification: *Neoregelia* hybrid×(*Neoregelia carcharodon*×*Neoregelia carolinae*) 'Seduction'.

Parentage:

*Female, or seed, parent.*—*Neoregelia* hybrid 'Autumn Leaves', not patented.

*Male, or pollen, parent.*—Unnamed proprietary selection of *Neoregelia carcharodon*×*Neoregelia carolinae,* not patented.

Propagation:

*Type.*—By offsets.

*Time to initiate roots, summer.*—About 30 days at 30° C. to 32° C.

*Time to initiate roots, winter.*—About 45 days at 30° C. to 32° C.

*Time to produce a rooted young plant, summer.*—About three to four months at 30° C. to 32° C.

*Time to produce a rooted young plant, winter.*—About four to five months at 18° C. to 22° C.

*Root description.*—Medium in thickness, fibrous; yellow to tan in color.

*Rooting habit.*—Moderately freely branching; medium density.

Plant description:

*Plant form/growth habit.*—Upright and outwardly arching growth habit; rosette leaves are erect when young, becoming outwardly arching with development; plants readily produce uniform offsets; vigorous growth habit.

*Plant height.*—About 18 cm.

*Plant diameter or spread.*—About 28 cm.

*Internode length.*—About 3.5 mm.

*Stem texture.*—Smooth, glabrous.

*Stem color.*—Close to NN155B.

Foliage description:

*Arrangement.*—Rosette, spiral phyllotaxis; simple; sessile, clasping.

*Shape.*—Oblong.

*Apex.*—Cuspidate.

*Base.*—Truncate.

*Margin.*—Serrate; spinose.

*Length.*—About 28.5 cm.

*Width, mid-section.*—About 8.4 cm.

*Width, base.*—About 10.8 cm.

*Texture.*—Smooth, glabrous; leathery.

*Luster.*—Glossy.

*Venation pattern.*—Parallel.

*Color.*—Lower leaves, upper surface: Close to 60C; towards the apex, close to N199A; towards the base, close to 185B; longitudinal stripes, close to 61A; venation, close to N199A. Lower leaves, lower surface: Close to 185A to 185C; venation, close to 71B. Upper leaves, upper surface: Close to 60B; towards the base, close to 155C; venation, close to 60B. Upper leaves, lower surface: Close to 71B; venation, close to 71B.

Inflorescence description:

*Inflorescence form.*—Terminal flat-topped compact corymb located inside the leaf rosette; about 86 flowers develop per inflorescence.

*Time to flower.*—Plants begin flowering about ten to twelve weeks after planting; plants flower naturally during the spring in Florida.

*Flower longevity.*—Individual flowers last about one day on the plant; flowers persistent.

*Fragrance.*—None detected.

*Inflorescence length.*—About 7 cm.

*Inflorescence diameter.*—About 4.5 cm.

*Flower size.*—Length: About 5.6 cm. Diameter: About 7 mm.

*Flower buds.*—Length: About 4.8 cm. Diameter: About 7 mm. Shape: Narrowly elongate. Color: Close to 93B to 93C.

*Petals.*—Quantity per flower: Three in a single whorl. Shape: Oblanceolate. Apex: Acuminate. Base: Truncate. Margin: Entire. Length: About 4.3 cm. Width: About 8 mm. Texture: Smooth, glabrous. Color: When opening, upper surface: Close to NN155D; towards the apex, close to 93B. When opening, lower surface: Close to NN155D; towards the apex, close to N89C. Fully opened, upper surface: Close to NN155D; towards the apex, close to 93A and 93B. Fully opened, lower surface: Close to NN155D; towards the apex, close to 93A.

*Flower bracts.*—Quantity per flower: One. Shape: Oblanceolate. Length: About 3.5 cm. Width: About 1 cm. Texture: Membraneous. Color: Close to 145C to 145D.

*Sepals.*—Quantity per flower: Three in a single whorl. Shape: Oblanceolate. Apex: Acuminate. Base: Truncate. Margin: Entire. Length: About 2.5 cm. Width: About 1 cm. Texture: Smooth, glabrous. Color, upper and lower surfaces: Close to 146D; towards the apex, close to 146C; towards the base, close to 187D.

*Peduncles.*—Length: About 9 mm. Diameter: About 1.4 cm. Strength: Strong. Aspect: Typically erect. Texture: Smooth, glabrous. Color: Close to NN155A.

*Pedicels.*—Length: About 6 mm. Diameter: About 5 mm. Strength: Strong. Aspect: Typically erect to somewhat outward and curving upright. Texture: Smooth, glabrous. Color: Close to 155C.

*Stamens.*—Quantity per flower: Six. Filament length: About 2.2 cm; partially adnate to the petals. Filament color: Close to NN155D. Anther shape: Lanceolate. Anther length: About 6 mm. Anther color: Close to 158D. Pollen amount: Moderate. Pollen color: Close to 158B.

*Pistils.*—Quantity per flower: One. Pistil length: About 4.4 cm. Stigma shape: Oval, elongated. Stigma color: Close to NN155C. Style length: About 2.3 cm. Style color: Close to NN155D. Ovary color: Close to NN155C.

*Fruit/seed.*—Fruit and seed production have not been observed on plants of the new *Neoregelia.*

Temperature tolerance: Plants of the new *Neoregelia* have been observed to tolerate temperatures ranging from about 2° C. to about 37° C.

Interior & garden performance: Plants of the new *Neoregelia* have been observed to have good postproduction longevity under interior conditions and to have good garden performance.

Disease/pest resistance: Plants of the new *Neoregelia* have been observed to be resistant to *Exserohilium.* Resistance to pests and other pathogens common to *Neoregelia* plants has not been observed.

It is claimed:

1. A new and distinct *Neoregelia* plant named 'Seduction' as illustrated and described.

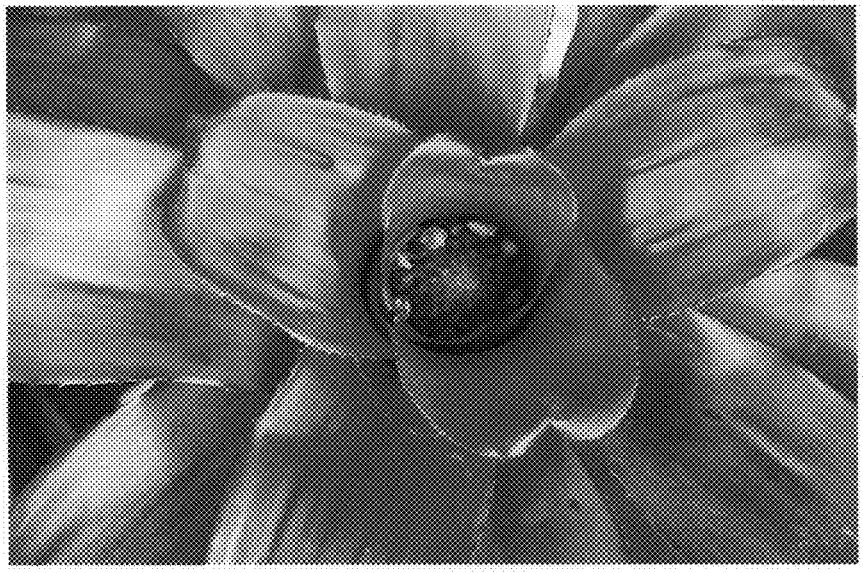
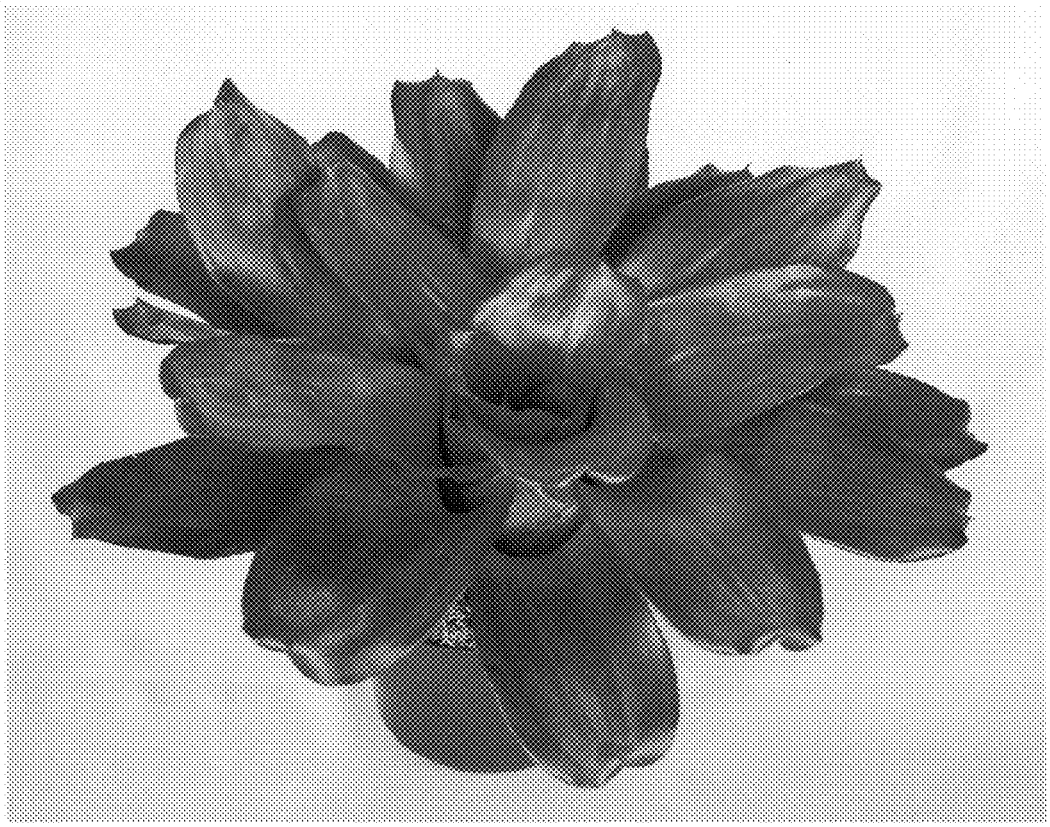

* * * * *